(12) United States Patent
Ikeda et al.

(10) Patent No.: US 12,265,070 B2
(45) Date of Patent: Apr. 1, 2025

(54) SENSOR SYSTEM AND FAILURE DETECTION METHOD FOR SENSOR SYSTEM

(71) Applicants: HONDA MOTOR CO., LTD., Tokyo (JP); NGK Spark Plug Co., LTD., Nagoya (JP)

(72) Inventors: Akitsugu Ikeda, Tokyo (JP); Michinori Tani, Tokyo (JP); Yuzo Higuchi, Nagoya (JP); Satoru Abe, Nagoya (JP)

(73) Assignees: HONDA MOTOR CO., LTD., Tokyo (JP); NITERRA CO., LTD., Nagoya (JP)

( * ) Notice: Subject to any disclaimer, the term of this patent is extended or adjusted under 35 U.S.C. 154(b) by 619 days.

(21) Appl. No.: 17/526,537

(22) Filed: Nov. 15, 2021

(65) Prior Publication Data

US 2022/0155272 A1    May 19, 2022

(30) Foreign Application Priority Data

Nov. 17, 2020   (JP) ................................ 2020-191179

(51) Int. Cl.
*G01N 33/00* (2006.01)
*G01M 15/10* (2006.01)
(Continued)

(52) U.S. Cl.
CPC .......... *G01N 33/007* (2013.01); *G01R 19/10* (2013.01); *G01R 31/10* (2013.01); *G01M 15/104* (2013.01)

(58) Field of Classification Search
CPC ... G01N 33/007; G01M 15/104; G01R 31/00; G01R 19/10
See application file for complete search history.

(56) References Cited

U.S. PATENT DOCUMENTS 9,086,393 B2 * 7/2015 Yazawa .............. G01N 33/0037
9,217,726 B2 * 12/2015 Ishiguro ............. G01N 27/4162
(Continued)

FOREIGN PATENT DOCUMENTS

JP    2016070882 A    5/2016

OTHER PUBLICATIONS

Texas Instruments: Understanding Data Converters (Year: 1995).*

*Primary Examiner* — Farhana A Hoque
*Assistant Examiner* — Joseph O Nyamogo
(74) *Attorney, Agent, or Firm* — Leason Ellis LLP; Melvin C. Garner; Mitsuhiro Haraguchi

(57) ABSTRACT

A sensor system includes a sensor element to which a control current is inputted, a DA converter to output the control current, and a control part configured to generate a control current instruction value and input the control current instruction value to the DAC, and further includes an instruction value generation part to sequentially generate an inspection current instruction value to be inputted to the DAC instead of the control current instruction value, an inspection current detection part to detect an inspection current value of an inspection current, an expected value calculation part to calculate an inspection current expected value, a difference value acquisition part to acquire a difference value between the inspection current value and the inspection current expected value, and a failure detection part to detect a failure of a bit in the DA converter, by frequency analysis of a temporal change of the difference value.

12 Claims, 6 Drawing Sheets

(51) Int. Cl.
    *G01R 19/10*     (2006.01)
    *G01R 31/10*     (2006.01)

(56) References Cited

U.S. PATENT DOCUMENTS

2014/0238853 A1* 8/2014 Yoshida ............. G01N 33/0037
                                                                     204/401
2016/0097738 A1   4/2016 Higuchi et al.
2018/0306136 A1* 10/2018 Mitsuno ............. F02D 41/1477

* cited by examiner

SENSOR SYSTEM AND FAILURE DETECTION METHOD FOR SENSOR SYSTEM

CROSS-REFERENCE TO RELATED APPLICATIONS

This application is based upon and claims the benefit of priority to the Japanese Patent Application No. 2020-191179, filed Nov. 17, 2020, the entire content of which is incorporated herein by reference.

FIELD OF THE INVENTION

The present invention relates to a sensor system that includes a sensor element, a DA converter which outputs a control current toward the sensor element, and a control part which generates a control current instruction value corresponding to the magnitude of the control current and inputs the control current instruction value to the DA converter, and a failure detection method for the sensor system.

BACKGROUND OF THE INVENTION

Conventionally, an air-fuel ratio sensor system which is mounted on a vehicle or the like and which detects the oxygen concentration of exhaust gas and detects the air-fuel ratio of an internal combustion engine, a NOx sensor system which is mounted on a vehicle or the like and which detects the concentration of NOx gas in exhaust gas, etc., are known.

Conventionally, an air-fuel ratio sensor system which is mounted on a vehicle or the like, which detects the oxygen concentration of exhaust gas and detects the air-fuel ratio of an internal combustion engine, and in which a gas sensor element having two cells, an oxygen pump cell and an oxygen concentration detection cell, is used, a NOx sensor system in which a gas sensor element having a cell for detecting the concentration of NOx gas in addition to the above two cells is used, etc., are known.

Among such sensor systems, there is a type of sensor system in which, in order to facilitate processing, control that is conventionally performed using an analog circuit is digitized, a control current instruction value is generated by a control part, and a control current is generated by a current DA converter and inputted to a sensor element. For example, as such a sensor system, the gas sensor system described in Japanese Laid-Open Patent Publication No. 2016-70882, etc., can be exemplified. In such a sensor system, if the magnitude of the control current inputted from the current DA converter to the sensor element is desired to be known, the control current instruction value, which is a digital value, is considered and used as the magnitude of the control current without measuring the control current that is actually flowing. For example, the control current instruction value is transmitted as the magnitude of the control current to an ECU or the like. This is because the magnitude of the control current outputted from the current DA converter (hereinafter, also referred to simply as DA converter or DAC) corresponds to the control current instruction value inputted to the DAC.

Here, the current DA converter is a type of DA converter that outputs a current with a magnitude corresponding to an inputted binary value of a predetermined number of bits (binary code: example: 14-bit signed integer). In the output stage of the DAC, current sources and switching elements (FETs, transistors, etc.), the number of which is a number corresponding to the resolution (bit depth, number of bits) of the DAC and which are weighted according to bits, are connected in parallel. Therefore, for example, in a 12-bit unsigned integer DAC (resolution: 12 bits), 12 (12 sets of) switching elements are provided in parallel, and in the output stage of a 14-bit signed integer (sign 1 bit+mantissa part 13 bits) DAC (resolution: 13 bits), 13 pairs (13 sets) of switching elements and positive current sources and 13 pairs (13 sets) of switching elements and negative current sources are provided in parallel.

RELATED ART DOCUMENTS

Patent Literature

Patent Literature 1: Japanese Laid-Open Patent Publication No. 2016-70882

Technical Problem

Meanwhile, one of the switching elements included in the output stage of this DAC may fail. Specifically, one of the switching elements of the output stage corresponding to the respective bits may cause a problem that the switching element is constantly ON (hereinafter, also referred to as "ON-failure") or a problem that the switching element is constantly OFF (hereinafter, also referred to as "OFF-failure"). In this case, the control current outputted from the DAC becomes an abnormal value by the magnitude corresponding to the bit (digit) corresponding to the switching element that has failed. For example, a description will be given with a 4-bit unsigned integer DAC.

For example, when the control current instruction value is inputted to the DAC in the order of (0000), (0010), and (1110), and when there is no failure in the DAC, the magnitude of the outputted control current is a magnitude corresponding to a value of "0, 2, 14". However, for example, when the switching element corresponding to the 3rd bit (the third bit from the least significant bit; hereinafter, the nth bit refers to the nth bit from the least significant bit) has caused "ON-failure", the DAC behaves as if the control current instruction value was inputted in the order of (0100), (0110), and (1110), that is, the DAC outputs a control current having a magnitude corresponding to a value of "4, 6, 14". When a code in which the failed 3rd bit is "1" (example: (1110) described above) is inputted, it seems as if a correct control current is outputted. On the other hand, for example, when the switching element corresponding to the 3rd bit has caused "OFF-failure", in contrast to the above "ON-failure", the DAC behaves as if the control current instruction value was inputted in the order of (0000), (0010), and (1010). That is, the DAC outputs a control current having a magnitude corresponding to a value of "0, 2, 10".

However, in the sensor system described in Japanese Laid-Open Patent Publication No. 2016-70882, even when one of the switching elements included in the output stage of the DAC has caused a failure (hereinafter, ON-failure and OFF-failure are collectively referred to as "bit failure"), this failure cannot be detected. This is because the control current instruction value inputted to the DAC and transmitted to the ECU or the like is a normal value regardless of the presence or absence of a failure of the DAC.

The present invention has been made in view of the above-described problems, and an object of the present invention is to provide: a sensor system that includes a sensor element, a DA converter which outputs a control current toward the sensor element, and a control part which generates a control current instruction value and inputs the control current instruction value to the DA converter and that allows a failure of the DA converter to be detected; and a detection method of a failure of the sensor system.

SUMMARY OF THE INVENTION

Solution to Problem

An aspect of the present invention is directed to a sensor system including: a sensor element to which a control current is inputted; a DA converter configured to output the control current toward the sensor element; a control part configured to generate a control current instruction value corresponding to a magnitude of the control current and input the control current instruction value to the DA converter; an instruction value generation part configured to sequentially generate an inspection current instruction value, which is to be inputted to the DA converter and which is changed in steps of a magnitude of 1 LSB from a first inspection current instruction value generated first to a final inspection current instruction value generated last, every predetermined generation cycle; an inspection current detection part configured to detect an inspection current value of an inspection current outputted from the DA converter to which the inspection current instruction value is inputted; an expected value calculation part configured to calculate an inspection current expected value, which is an expected value of the inspection current value expected to be detected by the inspection current detection part, by the inspection current instruction value being inputted to the DA converter; a difference value acquisition part configured to acquire a difference value between the detected inspection current value and the calculated inspection current expected value, corresponding to the same inspection current instruction value; and a failure detection part configured to detect a failure of a bit of the DA converter by frequency analysis of a temporal change of the sequentially obtained difference value.

Another aspect of the present invention is directed to a failure detection method for a sensor system including a sensor element to which a control current is inputted, a DA converter configured to output the control current toward the sensor element, and a control part configured to generate a control current instruction value corresponding to a magnitude of the control current and input the control current instruction value to the DA converter, the failure detection method including: an instruction value generating of sequentially generating an inspection current instruction value, which is changed in steps of a magnitude of 1 LSB from a first inspection current instruction value generated first to a final inspection current instruction value generated last, every predetermined generation cycle; an inputting of sequentially inputting the inspection current instruction value to the DA converter; an inspection current detecting of detecting an inspection current value of an inspection current outputted from the DA converter; an expected value calculating of calculating an inspection current expected value, which is an expected value of the inspection current value expected to be detected by the inspection current detection part, by the inspection current instruction value being inputted to the DA converter; a difference value acquiring of acquiring a difference value between the detected inspection current value and the calculated inspection current expected value, corresponding to the same inspection current instruction value; and a failure detecting of detecting a failure of a bit of the DA converter by frequency analysis of a temporal change of the sequentially obtained difference value.

In the above-described sensor system and the above-described failure detection method for the sensor system, the inspection current instruction value, which is generated every generation cycle by the instruction value generation part so as to be changed in steps of a magnitude of 1 LSB, is inputted to the DA converter, to which the control current instruction value is normally inputted from the control part, instead of the control current instruction value, and the inspection current corresponding to the inspection current instruction value is outputted from the DA converter. It should be noted that the case where the inspection current instruction value is equal to the control current instruction value is also acceptable. Then, the inspection current detection part detects the value of the inspection current that is actually flowing. On the other hand, the expected value calculation part calculates the inspection current expected value of the inspection current value expected to be detected by the inspection current detection part. Furthermore, the difference value acquisition part acquires the difference value between the inspection current value and the inspection current expected value.

When the DAC is normal, no difference occurs between the inspection current value and the expected inspection current value, and the difference value is 0 (in the ideal case where noise can be ignored) or a minute value within a measurement error near 0. The same also applies to the case where the inspection current instruction value changed in steps of a magnitude of 1 LSB is sequentially inputted to the DAC every generation cycle. That is, the difference value remains 0 or becomes a minute value within the measurement error near 0 even when time passes. In the following, 0 or a minute value within the measurement error near 0 is represented as "0±", and, for example, it is represented that "the difference value becomes 0±".

However, a switching element that turns on/off a current source that forms any one of the bits of the DAC may have caused a "bit failure". That is, in the case where the DAC is, for example, an unsigned positive current DA converter, a switching element for a positive current source that forms the respective bits may have caused a bit failure. In addition, in the case where the DAC is a signed DA converter, the switching element on the positive current source side or negative current source side that forms the respective bits may have caused a bit failure.

In these cases, when the inspection current instruction value changed in steps of a magnitude of 1 LSB is sequentially inputted to the DAC every generation cycle, the timing at which the bit that has caused the bit failure (hereinafter, this bit is also referred to as "fault bit") changes "from 1 to 0" or "from 0 to 1" appears periodically. Thus, when the difference value between the inspection current value and the expected inspection current value is taken and the temporal change of the difference value is seen, a period when the difference value is 0± and a period when the difference value is a predetermined value appear alternately and periodically. That is, a square wave pulse having a predetermined cycle is obtained. Therefore, when frequency analysis is performed on the square wave pulse and the fundamental frequency (or fundamental cycle) of the square wave pulse is obtained, the bit which has caused the bit failure can be detected based on the fundamental frequency. Thus, a sensor system that can detect a failure of a DAC such as the presence/absence of a bit failure of the DAC and the identification of the fault bit, and a failure detection method, for a sensor system, which allows a failure to be appropriately detected, are provided.

In the case where there are a plurality of fault bits, the shape of a square wave pulse obtained from a temporal change of a difference value becomes complicated. In this case as well, it may be possible to detect a plurality of fault bits by examining each frequency component included in the square wave pulse through frequency analysis of the square wave pulse.

Moreover, when it is determined whether the difference value is positive or negative, it can also be determined whether the fault bit has caused "ON-failure" or "OFF-failure".

Here, sequentially generating the "inspection current instruction value which is changed in steps of a magnitude of 1 LSB from a first inspection current instruction value generated first to a final inspection current instruction value generated last" refers to, for example, generating an inspection current instruction value in the order of (000000001000), (000000001001), (000000001010), . . . , (000011111111) by increasing the inspection current instruction value in steps of a magnitude of 1 LSB, for example, from (000000001000) to (000011111111), in the case where the DAC is, for example, a signed 12-bit DA converter, the most significant bit (MSB) is a sign bit, and the resolution (bit depth) is 11 bits. In this case, the "first inspection current instruction value" is (000000001000), and the "final inspection current instruction value" is (000011111111).

Preferably, a sequence of the "inspection current instruction value which is changed in steps of a magnitude of 1 LSB from a first inspection current instruction value to a final inspection current instruction value" which is suitable for detecting whether or not a specific bit or a bit in a specific range has caused a failure is generated in the instruction value generation part according to a bit (for example, 3rd bit) or bit range (for example, range of 1st to 4th bits) for which a fault is desired to be detected, since the inspection time can be shortened.

Moreover, FFT (Fast Fourier Transform) analysis can be adopted as the method for the frequency analysis of the temporal change of the difference value in the failure detection part.

As a sequence of the "inspection current instruction value which is sequentially changed in steps of a magnitude of 1 LSB", an inspection current instruction value which changes (increases or decreases) by a magnitude of 1 LSB every clock, such as (000000000000), (000000000001), (000000000010), . . . , (111111111111), can be generated with a period of one clock being set as a generation cycle. In addition, a sequence of an inspection current instruction value which is changed (increased or decreased) by a magnitude of 1 LSB every multiple clocks (every 3 clocks indicated below), such as (000000000000), (000000000000), (000000000000), (000000000001), (000000000001), (000000000001), (000000000010), . . . , may be used. In this case, the period of 3 clocks corresponds to the generation cycle.

Furthermore, in order to detect the inspection current value of the inspection current with the inspection current detection part, the voltage generated in a current conversion resistor through which the inspection current flows and whose resistance value is known is preferably read by the AD converter to obtain the inspection current value.

Moreover, all bits of the inspection current instruction value to be inputted to the DAC (all bits other than the sign bit (most significant bit) in the case where a signed integer is used) are divided into a low-order bit group close to the least significant bit (LSB) and a high-order bit group close to the most significant bit (for example, all 13 bits other than the sign bit are divided into a group of the 1st to 7th bits and a group of the 8th to 13th bits). Among these bits, for the bits belonging to the low-order bit group (for example, the bits belonging to the group of the 1st to 7th bits in the above example), failure detection is preferably performed by using the present technology.

That is, in the above-described sensor system, the bit whose failure is detected by the failure detection part is preferably a bit belonging to a low-order bit group in the DA converter.

Alternatively, in the above-described failure detection method for the sensor system, the bit whose failure is detected in the failure detection step is preferably a bit belonging to a low-order bit group in the DA converter.

When a switching element of a bit belonging to the low-order bit group in the DAC has caused a bit failure, the difference between the current value that should have been originally obtained and the current value that is actually obtained is small, so that failure detection is easily influenced by noise. Therefore, by detecting, only about once or twice, the difference between the current value that should have been originally obtained and the current value that is actually obtained, it may be difficult to reliably determine the presence/absence of a bit failure (ON-failure or OFF-failure).

On the other hand, when a failure of a bit belonging to the low-order bit group is detected by the present technology, after the difference between the current value that should have been originally obtained and the current value that is actually obtained is obtained a considerable number of times such that a frequency can be detected by frequency analysis, frequency analysis can be performed, so that the influence of noise can be suppressed and the presence/absence of a failure can be appropriately detected.

Among the bits belonging to the low-order bit group, particularly, for the 1st bit (least significant bit) or the 2nd bit for which the difference between the current value that should have been originally obtained and the current value that is actually obtained becomes small and is easily influenced by noise, the present technology is preferably used for detecting the presence/absence of a bit failure.

Furthermore, in any one sensor system described above, preferably, the sensor element has a sensor output terminal at which a sensor voltage is generated, the sensor system further comprises an AD converter configured to sequentially convert the sensor voltage generated at the sensor output terminal, into a sensor voltage value, the control part includes a PID calculation part configured to generate the control current instruction value by PID calculation using the sensor voltage value, and the instruction value generation part includes an input part configured to input a predetermined input constant value, instead of the sensor voltage value, to the PID calculation part of the control part, and an inspection coefficient setting part configured to set a coefficient Pc of a P term and a coefficient Dc of a D term in the PID calculation by the PID calculation part to 0, and to set a coefficient Ic of an I term to a magnitude which allows the inspection current instruction value, which is sequentially changed in steps of a magnitude of 1 LSB, to be outputted from the PID calculation part.

Alternatively, in any one failure detection method for the sensor system described above, preferably, the sensor element has a sensor output terminal at which a sensor voltage is generated, the sensor system includes an AD converter configured to sequentially convert the sensor voltage generated at the sensor output terminal, into a sensor voltage value, the control part includes a PID calculation part configured to generate the control current instruction value by PID calculation using the sensor voltage value, the instruction value generating includes: inputting a predetermined input constant value, instead of the sensor voltage value, to the PID calculation part of the control part; and setting a coefficient Pc of a P term and a coefficient Dc of a D term in the PID calculation to 0, and setting a coefficient Ic of an I term to a magnitude which allows the inspection current instruction value, which is sequentially changed in steps of 1 LSB, to be outputted from the PID calculation part, and the PID calculation part is caused to sequentially generate the inspection current instruction value.

In the sensor system and the failure detection method for the sensor system, in order to control the sensor, the PID calculation part of the control part performs PID calculation using the sensor voltage value, and generates the control current instruction value. In addition to this, in the instruction value generation part, the PID calculation part generates the inspection current instruction value using a predetermined input constant value instead of the sensor voltage value through change of each coefficient PC, etc. Therefore, it is not necessary to provide a circuit or the like for generating the inspection current instruction value separately from the calculation by the PID calculation part, and the inspection current instruction value which sequentially changes in steps of a magnitude of 1 LSB can easily be obtained.

Furthermore, any one failure detection method for the sensor system described above is preferably executed while an internal combustion engine having the sensor system mounted thereon is stopped.

In the present technology, the above-described failure detection method is executed not while the internal combustion engine having the sensor system mounted thereon is operating (for example, while a vehicle equipped with the internal combustion engine is driven), but while the internal combustion engine is stopped. Therefore, failure detection of the sensor system can be performed without influencing the operation of the internal combustion engine.

DETAILED DESCRIPTION OF THE INVENTION

Embodiment

Figure 1:
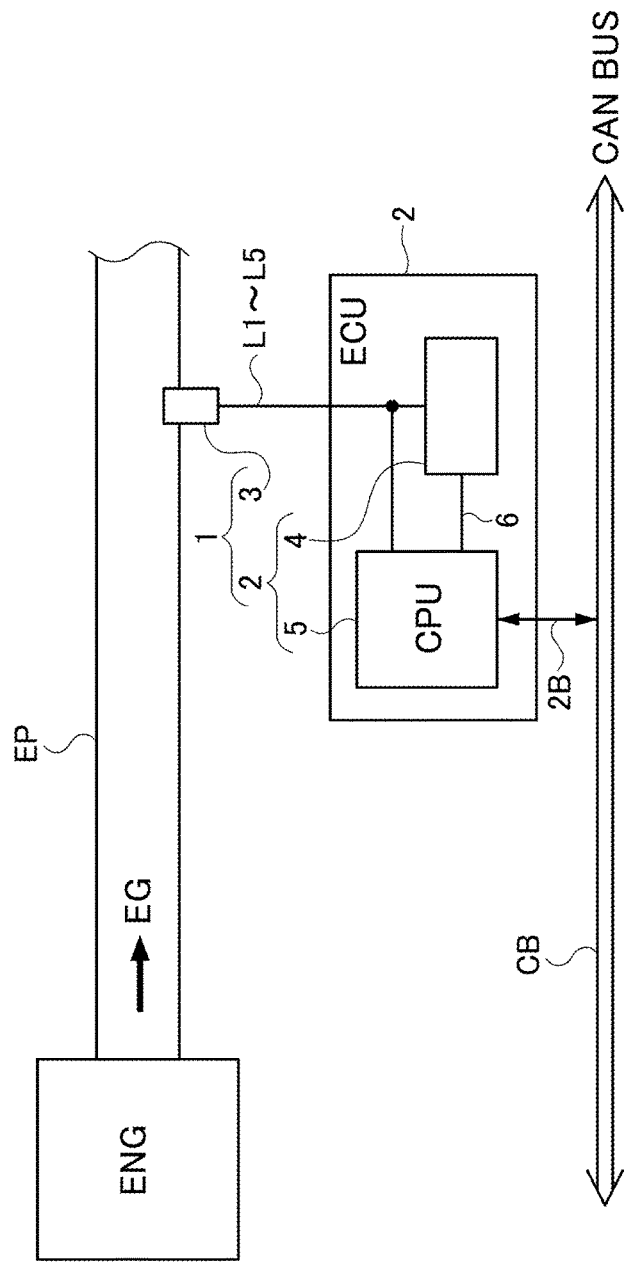
FIG. 1 is an explanatory diagram showing the overall configuration in the case where a gas sensor system according to an embodiment is used for controlling an internal combustion engine of a vehicle.
Figure 2:
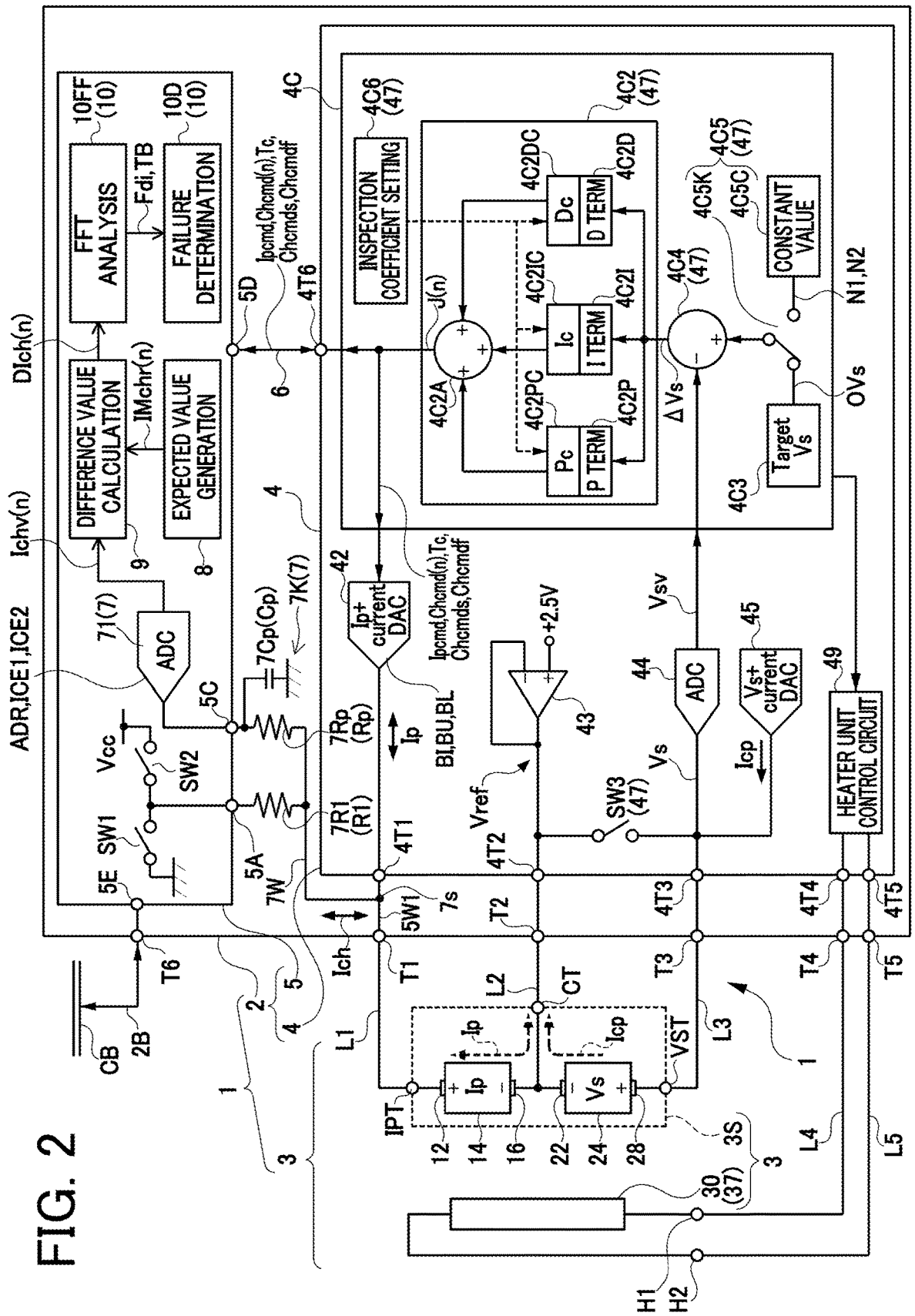
FIG. 2 is an explanatory diagram showing a schematic configuration of the gas sensor system according to the embodiment.

Hereinafter, an embodiment of the present invention will be described with reference to the drawings. FIG. 1 is a diagram showing the overall configuration in the case where a gas sensor system 1 according to the present embodiment is used for controlling an internal combustion engine of a vehicle. FIG. 2 is a diagram showing a schematic configuration of the gas sensor system 1.

The gas sensor system 1 includes: a gas detection part 3 which is mounted on an exhaust pipe EP of an engine ENG of a vehicle (not shown); and an ECU 2 which is connected to the gas detection part 3 via wires L1 to L5, which includes a sensor control circuit part 4 for controlling the gas detection part 3 and also includes a CPU 5, and which performs electronic control of the vehicle and the engine ENG. The ECU 2 (CPU 5) is connected to a CAN bus CB of the vehicle via a connection bus 2B, and can transmit and receive data to and from other ECUs, various sensors, and actuators.

Among these components, the gas detection part 3 and the sensor control circuit part 4 are an air-fuel ratio sensor (full-range air-fuel ratio sensor) which linearly detects the oxygen concentration (air-fuel ratio) of exhaust gas EG (gas to be measured) and which is used for air-fuel ratio feedback control in an internal combustion engine.

Among these components, the sensor control circuit part 4 included in the ECU 2 transmits and receives data of a control current instruction value Ipcmd indicating an oxygen concentration (air-fuel ratio), an inspection current instruction value Chcmd(n), etc., to and from the CPU 5 included similarly in the ECU 2, via a connection wire 6 connecting a terminal 4T6 of the sensor control circuit part 4 and a digital input terminal 5D of the CPU 5, etc., as described later.

The sensor control circuit part 4 is composed of an ASIC (Application Specific IC), and includes a control part 4C which controls a sensor element part 3S provided in the gas detection part 3 and which detects an oxygen concentration (air-fuel ratio) and the like, a DA converter 42, a reference potential generation circuit 43, a second AD converter 44, a minute current supply circuit 45, a heater part control circuit 49 which controls a heater part 30 provided in the gas detection part 3, etc.

Figure 3:
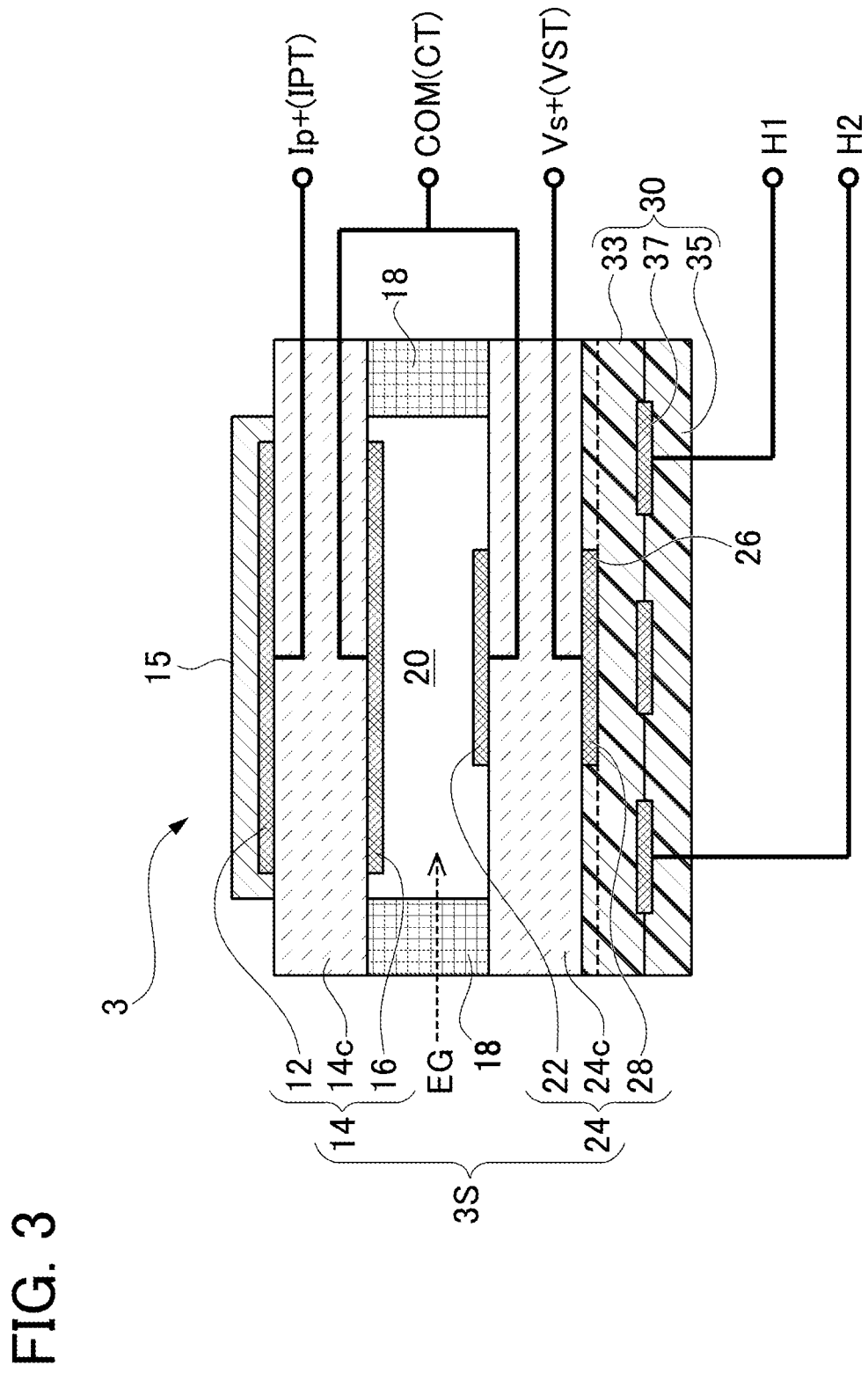
FIG. 3 is an explanatory diagram showing a schematic configuration of a sensor element part in a gas detection part of the gas sensor system according to the embodiment.

First, the configuration of the gas detection part 3 will be described. FIG. 3 is an explanatory diagram showing a schematic configuration of the gas detection part 3. The gas detection part 3 is a laminate in which an oxygen pump cell 14, a porous layer 18, and an oxygen concentration detection cell 24 are laminated in this order. The heater part 30 is further laminated on one side (lower side in FIG. 3) of the gas detection part 3.

In the oxygen pump cell 14, an electrolyte layer 14c made of a solid electrolyte having oxygen ion conductivity is used as a substrate, and a pair of electrodes 12 and 16 are formed on both surfaces of the electrolyte layer 14c. Similarly, in the oxygen concentration detection cell 24, an electrolyte layer 24c made of a solid electrolyte having oxygen ion conductivity is used as a substrate, and a pair of electrodes 22 and 28 (porous electrodes) are formed on both surfaces of the electrolyte layer 24c.

The porous layer 18 is interposed between the electrolyte layer 14c and the electrolyte layer 24c. A hollow measurement chamber 20 surrounded by the porous layer 18, the electrolyte layer 14c, and the electrolyte layer 24c is formed inside the porous layer 18 in the direction in which the porous layer 18 extends (inner side in the right-left direction in FIG. 3), and the exhaust gas EG can be introduced into the measurement chamber 20 via the porous layer 18. The porous layer 18 is a diffusion rate-determining layer that allows the exhaust gas EG to flow into the measurement chamber 20 and that limits the inflow rate of the exhaust gas EG.

In the measurement chamber 20, the second pump electrode 16 of the oxygen pump cell 14 and the second detection electrode 22 of the oxygen concentration detection cell 24 are exposed. These electrodes 16 and 22 are electrically conducted with each other and are connected to a COM terminal CT of the sensor element part 3S. In addition, the first pump electrode 12 of the oxygen pump cell 14 is connected to an Ip+terminal IPT, and the first detection electrode 28 of the oxygen concentration detection cell 24 is connected to a Vs+terminal VST.

Moreover, the entirety of the first pump electrode 12 of the oxygen pump cell 14 is covered with a protective layer 15 which suppresses poisoning of the first pump electrode 12. The protective layer 15 is formed of porous ceramic or the like, and the exhaust gas EG can reach the first pump electrode 12 through the protective layer 15.

The heater part 30 is laminated on the electrolyte layer 24c of the oxygen concentration detection cell 24, and has a configuration in which a heater resistor 37 formed of a conductor is interposed between a pair of alumina sheets 33 and 35. The heater resistor 37 is connected to heater terminals H1 and H2. By energizing the heater part 30 to increase the temperature of the sensor element part 3S, the electrolyte layers 14c and 24c of the sensor element part 3S are activated. Accordingly, oxygen ions are allowed to move in the electrolyte layers 14c and 24c. On the contrary, until the temperature of the sensor element part 3S becomes sufficiently high, such as when the vehicle is started (cold start), the electrolyte layers 14c and 24c are not activated and the present state is a state where oxygen ions cannot move in the electrolyte layers 14c and 24c (high resistance state where a pump current Ip does not flow)

The aluminum sheet 33 of the heater part 30 covers the entirety of the first detection electrode 28 of the oxygen concentration detection cell 24, thereby sealing the first detection electrode 28. Therefore, the space (pore) inside the first detection electrode 28 (porous electrode) forms a reference oxygen chamber 26 and functions as an internal oxygen reference source.

Next, the sensor control circuit part 4 of the gas sensor system 1 will be described with reference to FIG. 2. The sensor control circuit part 4 included in the ECU 2 has terminals 4T1 to 4T5, and these terminals 4T1, etc., are connected to each terminal IPT, etc., of the sensor element part 3S of the gas detection part 3 and the heater terminals H1 and H2 of the heater part 30 via terminals T1 to T5 and the first wire L1 to the fifth wire L5 of the ECU 2.

In addition to the control part 4C, the sensor control circuit part 4 includes a DAC 42 which is connected to the first terminal T1 through the terminal 4T1, the reference potential generation circuit 43 which is connected to the second terminal T2 through the terminal 4T2, and the second AD converter 44 and the minute current supply circuit 45 which are connected to the third terminal T3 through the terminal 4T3. Among these components, the DAC 42 causes a pump current Ip, which has a magnitude corresponding to a control current instruction value Ipcmd inputted from a later-described PID calculation part 4C2 in the control part 4C, to flow to the oxygen pump cell 14 of the sensor element part 3S via the first terminal T1 and the terminal IPT of the sensor element part 3S. In addition, the reference potential generation circuit 43 generates a reference potential Vref (2.5 V in this example) by a buffer circuit using an operational amplifier, and applies the reference potential Vref to the second pump electrode 16 and the second detection electrode 22 via the second terminal T2 and the COM terminal CT of the sensor element part 3S. The second AD converter 44 detects a detection cell voltage (sensor voltage) Vs generated between the second detection electrode 22 and the first detection electrode 28 of the oxygen concentration detection cell 24, via the Vs+terminal VST of the sensor element part 3S and the third terminal T3, performs AD conversion of the detection cell voltage (sensor voltage) Vs into a detection cell voltage value Vsv, and inputs the detection cell voltage value Vsv to the control part 4C. The output of the minute current supply circuit 45 which is composed of a DA converter (DAC) which causes a constant minute current Icp (=20 µA) and a current for detecting internal resistance to flow to the oxygen concentration detection cell 24 is also connected between the terminal 4T3 and the second AD converter 44. The minute current Icp caused to flow to the oxygen concentration detection cell 24 acts on the oxygen concentration detection cell 24 to pump the oxygen in the measurement chamber 20 into the first detection electrode 28 (porous electrode). Accordingly, the reference oxygen chamber 26 functions as an internal oxygen reference source.

The control part 4C controls the magnitude of the pump current Ip caused to flow to the oxygen pump cell 14, such that the detection cell voltage Vs generated at both ends of the oxygen concentration detection cell 24 (potential difference between the third terminal T3 and the second terminal T2 detected by the second AD converter 44) becomes a predetermined voltage, while causing such a constant minute current Icp to flow to the oxygen concentration detection cell 24. Accordingly, oxygen ions are pumped into or out from the measurement chamber 20 by the pump cell 14 such that the oxygen concentration of the exhaust gas EG introduced into the measurement chamber 20 through the porous layer 18 becomes a predetermined concentration.

In this control, the control part 4C performs PID control by a digital method. The current value and the current direction of the pump current Ip caused to flow to the oxygen pump cell 14 controlled by this PID control change according to the oxygen concentration (air-fuel ratio) of the exhaust gas EG introduced into the measurement chamber 20 through the porous layer 18. Therefore, the oxygen concentration of the exhaust gas EG can be detected from the magnitude of the pump current Ip. In addition, the sensor control circuit part 4 performs drive control of the gas sensor 2 (sensor element part 3S) by performing feedback-control of the pump current Ip caused to flow to the oxygen pump cell 14 through PID control such that the detection cell voltage Vs generated in the oxygen concentration detection cell 24 becomes a predetermined voltage.

In addition, the heater part control circuit 49 of the sensor control circuit part 4 is connected to the terminals 4T4 and 4T5, and these terminals 4T4 and 4T5 are connected to the heater terminals H1 and H2 of the heater part 30 of the sensor element part 3S via the fourth terminal T4 and the fifth terminal T5 and the fourth wire L4 and the fifth wire L5, respectively. Moreover, the heater part control circuit 49 is connected to the control part 4C, and performs PWM control of ON/OFF of energization to the heater part 30 according to an instruction from the control part 4C. The detailed description of the PWM control of the heater part 30 by the control part 4C is omitted.

Moreover, in the sensor control circuit part 4, a third switch SW3 is connected between the terminal 4T2 and the terminal 4T3. The third switch SW3 is normally turned off (opened), but at the time of failure inspection of the DAC 42 described later, the third switch SW3 is turned on to cause a short circuit therebetween, and the detection cell voltage Vs to be inputted to the second AD converter 44 is forcibly set to zero.

The feedback control by the PID control in the sensor control circuit part 4 will be described in detail. As shown in FIG. 2, the detection cell voltage Vs of the oxygen concentration detection cell 24 is inputted to the sensor control circuit part 4 through the terminals 4T2 and 4T3, the second terminal T2, and the third terminal T3, and is sequentially converted into a digital cell voltage value Vsv by the second AD converter 44.

For the cell voltage value Vsv inputted to the control part 4C, the difference from a target Vs value OVs which is held in a target Vs value input part 4C3 ($\Delta$Vs=OVs−Vsv: deviation from the target) is calculated by a difference part 4C4. Then, a difference value $\Delta$Vs ( . . . , $\Delta$Vs(n−1), $\Delta$Vs(n), $\Delta$Vs(n+1), . . . n is a natural number.) which is the difference between the target Vs value OVs and the cell voltage value Vsv is sequentially inputted to the PID calculation part 4C2 every clock.

The PID calculation part 4C2 includes a proportional calculation part 4C2P which calculates a P term, an integral calculation part 4C2I which calculates an I term, a differential calculation part 4C2D which calculates a D term, and an addition part 4C2A which obtains the sum of these terms. Each calculation part 4C2P, etc., have coefficient holding parts 4C2PC, 4C2IC, and 4C2DC which hold a proportional coefficient Pc, an integration coefficient Ic, and a differential coefficient Dc used for calculation.

Among these parts, the proportional calculation part 4C2P calculates a value obtained by multiplying the difference value $\Delta$Vs(n) by the proportional coefficient Pc. The integral calculation part 4C2I calculates the sum of a value obtained by multiplying the difference value $\Delta$Vs(n) by the integration coefficient Ic and the previously obtained I term Iout (n−1). In addition, the differential calculation part 4C2D calculates a value obtained by multiplying the difference obtained by subtracting the previously obtained difference value $\Delta$Vs(n−1) from the present difference value $\Delta$Vs(n), by the differential coefficient Dc. A PID calculation value J(n) is the sum of the P term, the I term, and the D term. When described using the difference value $\Delta$Vs(n), etc., the following equation (1) is established.

$$J(n)=Pout(n)+Iout(n)+Dout(n) \quad (1)$$

wherein
Pout(n)=Pc·$\Delta$Vs(n),
Iout(n)=Ic·$\Delta$Vs(n)+Iout(n−1), and
Dout(n)=Dc·($\Delta$Vs(n)−$\Delta$Vs(n−1)).

The control part 4C inputs the thus obtained PID calculation value J(n), which is a 14-bit signed integer, as the control current instruction value Ipcmd to the DAC 42. The DAC 42 outputs a positive or negative analog pump current (control current) Ip having a magnitude corresponding to the control current instruction value Ipcmd, toward the oxygen pump cell 14. Thus, the sensor element part 3S is subjected to feedback control through PID control by the control part 4C of the sensor control circuit part 4.

The control current instruction value Ipcmd indicates the magnitude of the pump current (control current) Ip outputted from the DAC 42, that is, the oxygen concentration (air-fuel ratio) of the exhaust gas EG. Therefore, the control current instruction value Ipcmd is separately inputted to the CPU 5 through the terminal 4T6, the connection wire 6, and the digital input terminal 5D and used for control of the engine ENG, etc., and is also sent to the CAN bus CB through an input/output terminal 5E, a sixth terminal T6, and the connection bus 2B and transmitted to another device.

As described above, the current DA converter 42 used in the present embodiment is a type of DA converter that outputs a current value corresponding to an inputted binary code (for example, 14-bit signed integer) of a predetermined number of bits. Instruction values such as the control current instruction value Ipcmd inputted to the DAC 42 are displayed in the sign-mantissa part form, and the most significant bit (MSB, for example, the 14th bit) is a sign bit. If the most significant bit is "0", it indicates a positive value, and if the most significant bit is "1", it indicates a negative value. On the other hand, a numerical value (absolute value) is indicated by 2's complement display using the sign for the lower 13 bits forming the mantissa part.

In the output stage of the DAC 42, a total of 13 pairs (13 sets) of a positive current source that outputs a positive current weighted according to each bit BI and a positive switching element that is connected in series with the positive current source and that interrupts the positive current, and a total of 13 pairs (13 sets) of a negative current source that outputs a negative current weighted according to each bit BI and a negative switching element that is connected in series with the negative current source and that interrupts the negative current, are connected in parallel, corresponding to the bit depth (13 bits) of the DAC.

The operation of the switching element that interrupts each current source corresponding to each bit BI is selected according to the sign bits (most significant bits) in the inputted control current instruction value Ipcmd and inspection current instruction value Chcmd.

Here, the bits BI forming a code to be inputted to the DAC 42 are divided into a high-order bit group BU and a low-order bit group BL except for the sign bit. For example, in a signed 2M bit code, the 2M−1 bits excluding the sign bit are divided into a low-order bit group BL, close to the 1st bit (least significant bit), from the 1st bit to the Mth bit, and a high-order bit group BU, close to the 2Mth bit, which is the most significant bit, from the M+1th bit to the 2M−1th bit (in the present embodiment, the 13 bits are divided into a low-order bit group BL of the 1st to 7th bits and a high-order bit group BU of the 8th to 13th bits). In the present embodiment, the presence/absence of a bit failure is detected for each bit BI belonging to the lower bit group BL (specifically, the 1st to 7th bits).

Figure 5:
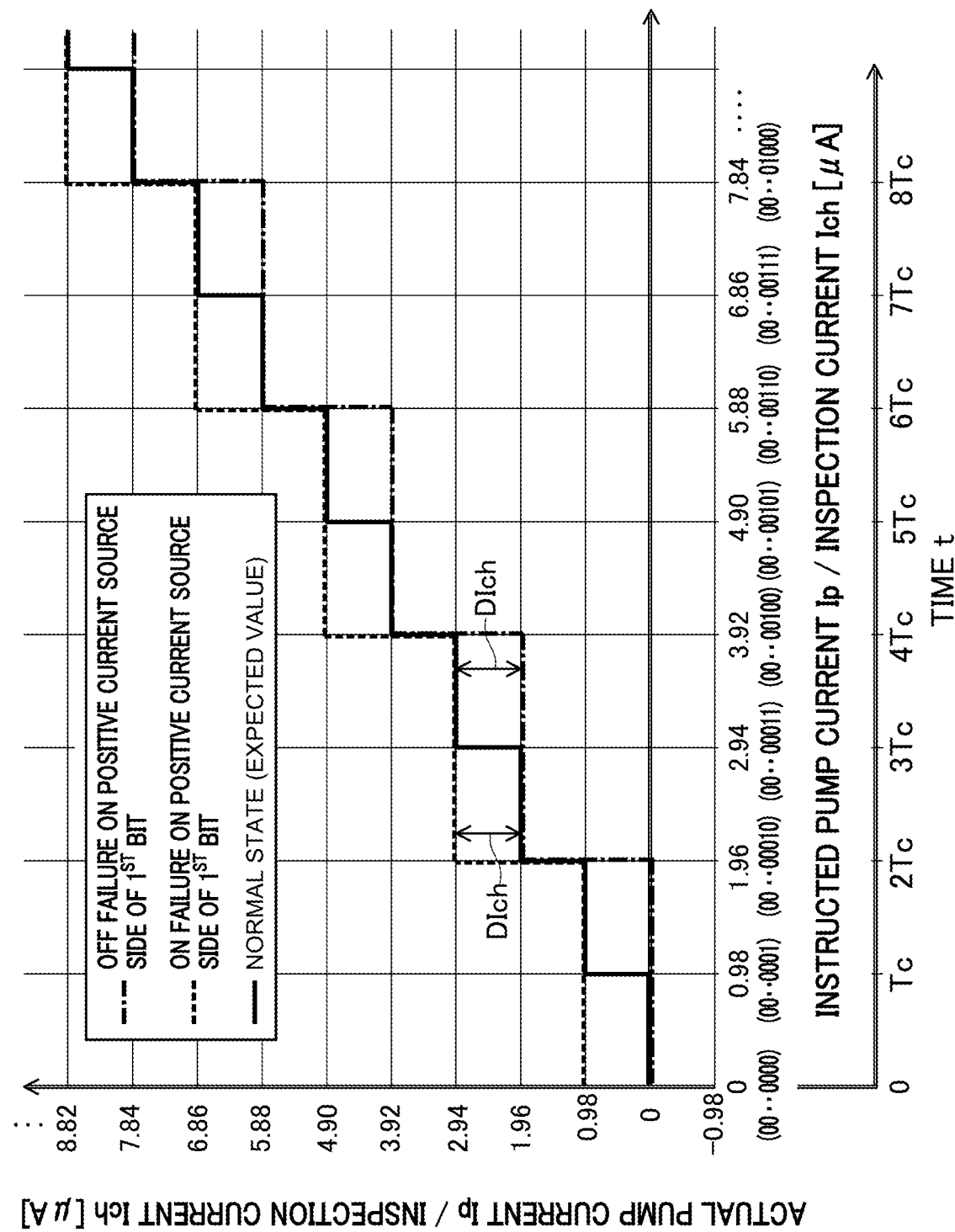
FIG. 5 is a graph showing the relationship between an instructed pump current Ip and inspection current Ich and an actually obtained pump current Ip and inspection current Ich in the case where the DAC is normal and in the case where the positive current source side of the 1st bit in an output stage has caused ON-failure or OFF-failure, in the gas sensor system according to the embodiment.

Next, the behavior of the pump current Ip when the DAC 42 fails will be described. As described above, the DAC 42 outputs an analog positive or negative pump current Ip according to an inputted binary code of predetermined resolution (bit depth, in the present embodiment, 13 bits), specifically, the control current instruction value Ipcmd represented by a 14-bit signed integer. However, the DAC 42 may fail. As the failure mode, "ON-failure" in which either one of the switching elements that each turn on and off the output of the positive current source or the negative current source corresponding to the respective bits in the output stage of the DAC 42 is constantly ON or "OFF-failure" in which either one of such switching elements is constantly OFF may occur. Then, the magnitude of the pump current Ip may become abnormal by the magnitude corresponding to the bit (digit) corresponding to the switching element that has failed. FIG. 5 is a graph in which the horizontal axis indicates a pump current Ip which the DAC 42 is instructed to output (which should have been originally obtained) and the vertical axis indicates a pump current Ip actually obtained by the DAC 42. This graph shows the relationship between both pump currents Ip, and a thick solid line extending stepwise from the origin to the upper right indicates the case where the DAC 42 is normal. In addition, a broken line indicates the case where "ON-failure" in which the positive switching element of the 1st bit is constantly ON occurs, and a chain-dotted line indicates the case where "OFF-failure" in which the same positive switching element of the 1st bit is constantly OFF occurs.

FIG. 5 shows the range of 0 or positive values where the sign bit (most significant bit) is 0, and shows, in an enlarged manner, only a part near the origin (range of current values 0 to about 9 µA) of a graph in the case where the range of integers (0 to 8191) indicated by the 13-bit mantissa part is caused to correspond to the range of current values 0 to 8000 µA of the pump current Ip or inspection current Ich outputted by the DAC 42.

Moreover, in FIG. 5, vertical scale lines are provided at the positions of 0, 0.98, 1.96, 2.94, 3.92, . . . (µA) which are integral multiples of an output current Io (specifically, Io=0.98 µA) corresponding to a magnitude of 1 LSB. These current values each correspond to a current value in which the sign of the 1st bit of a 14-bit instruction value shown below the current value is switched "from 0 to 1" or "from 1 to 0".

As can also be understood from the graph shown in FIG. 5, both in the case of "ON-failure" shown by the broken line and in the case of "OFF-failure" shown by the chain-dotted line, when the magnitude of the pump current Ip (control current instruction value Ipcmd) is increased or decreased, the case where the actual pump current Ip is equal to the value in the normal state and the case where the actual pump current Ip deviates greatly from the value in the normal state alternately occur. For example, as shown in FIG. 5, when the positive switching element of the 1st bit has caused "ON-failure", if the sign of the 1st bit of the control current instruction value Ipcmd is 1, a pump current Ip having a magnitude equal to that in the normal case shown by the thick solid line is outputted as shown by the broken line. On the other hand, if the sign of the 1st bit of the control current instruction value Ipcmd is 0, a pump current Ip larger than that in the normal case is outputted. This is because a pump current Ip that is excessive by the amount of current outputted by the positive current source corresponding to the 1st bit is outputted. On the contrary, when the positive switching element of the 1st bit has caused "OFF-failure", if the sign of the 1st bit of the control current instruction value Ipcmd is 0, a pump current Ip having a magnitude equal to that in the normal case shown by the thick solid line is outputted as shown by the chain-dotted line. On the other hand, if the sign of the 1st bit of the control current instruction value Ipcmd is 1, a pump current Ip smaller than that in the normal case is caused to flow. This is because a pump current Ip that is insufficient by the amount of current that should be outputted by the positive current source corresponding to the 1st bit is outputted. Therefore, as shown in FIG. 5, the magnitude of a difference value DIch which occurs between the actual pump current Ip and the pump current Ip in the normal state, that is, the instructed pump current Ip, is constant at 0.98 µA as an output current Io corresponding to a 2M-bit (specifically, 14-bit) binary code (00000000000001) in which only the 1st bit is 1.

Therefore, in the present embodiment, in order to detect a failure of the DAC 42, the inspection current instruction value Chcmd inputted to the DAC 42 instead of the control current instruction value Ipcmd is set as the following value, and a failure of the DAC 42 is detected. That is, as a 14-bit inspection current instruction value Chcmd, for example, an inspection current instruction value Chcmd(n) that is sequentially changed from a first inspection current instruction value Chcmds (for example, (00000000000000)) to a final inspection current instruction value Chcmdf (for example, (00000001111111)) in steps of a magnitude of 1 LSB, such as (00000000000000), (00000000000001), (00000000000010), . . . , (00000001111111), is generated every generation cycle Tc and inputted to the DAC 42. As will be described later, such generation of the inspection current instruction value Chcmd (n) every generation cycle Tc is performed by an instruction value generation part 47 (specifically, PID calculation part 4C2, etc.) in the control part 4C.

Then, when the DAC 42 has not failed, as shown by the thick solid line in FIG. 5, the inspection current Ich which rises stepwise and linearly from the first inspection current instruction value Chcmds (for example, (00000000000000): corresponding to 0 µA) to the final inspection current instruction value Chcmdf (for example, (00000001111111): corresponding to 124 µA) is outputted from the DAC 42. As described above, even when the inspection current instruction value Chcmd(n) is inputted to the DAC 42 and the inspection current Ich is outputted from the DAC 42, the relationship between the instructed inspection current Ich and the inspection current Ich that actually flows is the relationship shown in FIG. 5. Moreover, since the inspection current instruction value Chcmd(n) which is sequentially changed in steps of a magnitude of 1 LSB is generated every generation cycle Tc, FIG. 5 can also be understood as a graph of a temporal change of the inspection current Ich actually obtained by the DAC 42, wherein the horizontal axis in FIG. 5 is changed to a horizontal axis indicating the passage of time t as shown in the lower part. In this case, the timing at which the 1st bit is switched "from 0 to 1" or "from 1 to 0" comes every generation cycle Tc.

Figure 6:
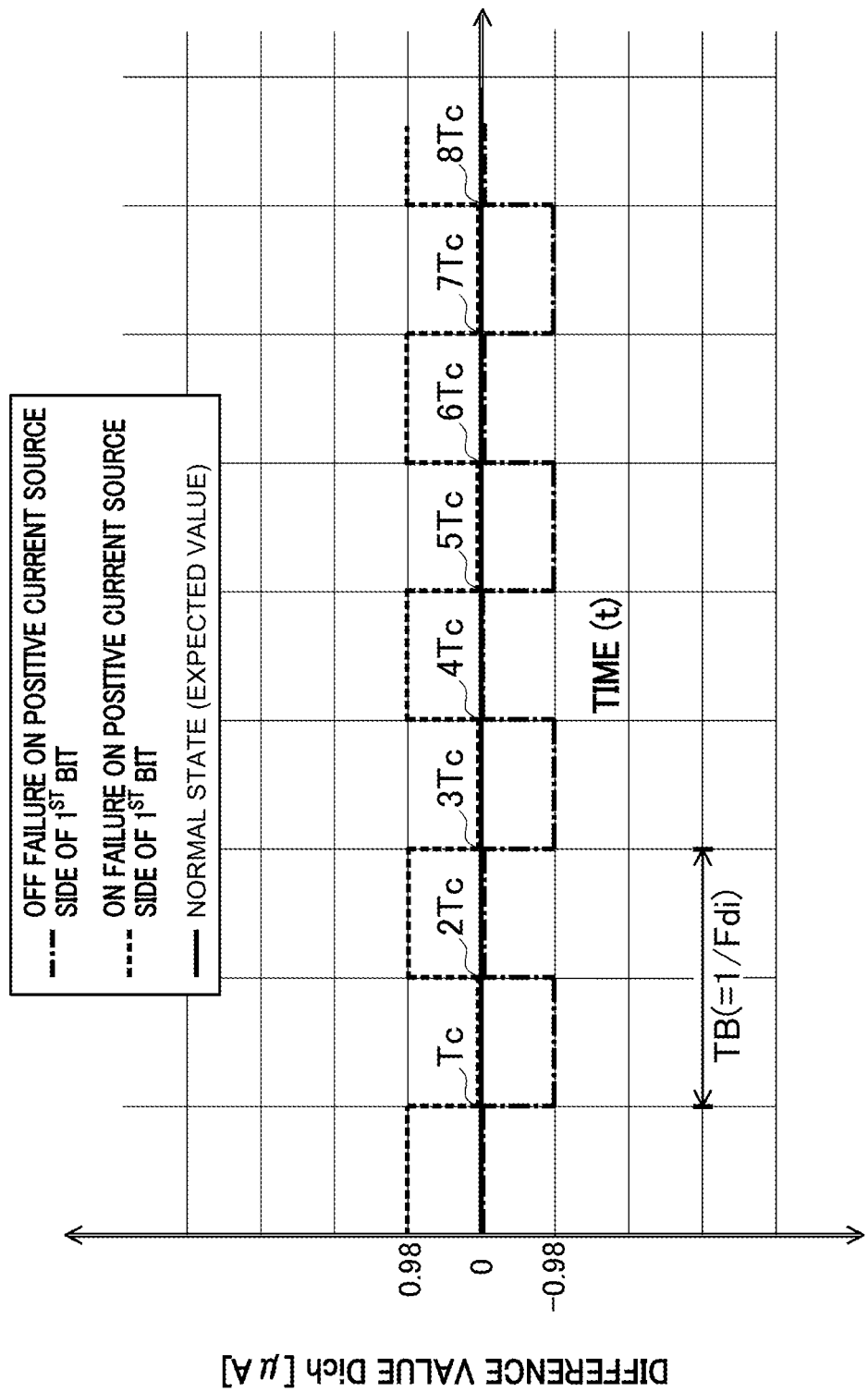
FIG. 6 is a graph showing a temporal change of a difference value obtained in the case of FIG. 5.

Therefore, when the difference value DIch which occurs between the actual inspection current Ich and the instructed inspection current Ich is calculated, the temporal change thereof is a result shown in FIG. 6. That is, in the normal case shown by the thick solid line, the difference value DIch is 0 or a minute value within the measurement error (difference value DIch=0±) at any timing. However, when the positive switching element corresponding to the 1st bit has caused "ON-failure" (broken line) or "OFF-failure" (alternate long and short dash line), a waveform of a square wave pulse having a fundamental cycle TB (=2Tc) and a fundamental frequency Fdi (=1/TB=1/2Tc) in which the difference value DIch alternates between 0 µA and 0.98 µA (or 0 µA and −0.98 µA) every time the time t elapses by Tc, is formed.

In FIG. 5 and FIG. 6, the case where the positive switching element on the positive current source side of the 1st bit has caused "ON-failure" or "OFF-failure" in the DAC 42 to which the control current instruction value Ipcmd or inspection current instruction value Chcmd(n) which is a binary code of a 14-bit signed integer is inputted, is shown.

However, as can easily be understood, even when the positive switching element corresponding to a bit BI (any of the 1st bit to the 13th bit) forming the mantissa part excluding the sign bit has caused "ON-failure" or "OFF-failure", the same result is obtained.

It should be noted that the magnitude of the difference value DIch and the magnitudes of the fundamental cycle TB and the fundamental frequency Fdi are different depending on which of the 1st bit to the 13th bit is the fault bit. For example, when the positive switching element corresponding to the 4th bit has caused "ON-failure" or "OFF-failure", a waveform of a square wave pulse having a fundamental cycle TB (=16Tc) and a fundamental frequency Fdi (=1/TB=1/16Tc) in which the difference value DIch alternates between 0 μA and 7.8 μA (or 0 μA and −7.8 μA) every time the time t elapses by eight times of the generation cycle Tc, is formed.

Therefore, if the temporal change (square wave pulse) of the difference value DIch is acquired and the fundamental frequency Fdi (=1/TB) or the fundamental cycle TB thereof is obtained by frequency analysis, the bit to which the positive switching element, of the DAC 42, having caused "ON-failure" or "OFF-failure" corresponds, can be detected.

In FIG. 5 and FIG. 6, the case where the positive switching element of the 1st bit forming the mantissa part has caused "ON-failure" or "OFF-failure" in the DAC 42 is shown.

However, the same can also be considered when the negative switching element corresponding to the 1st bit has caused "ON-failure" or "OFF-failure" in the DAC 42. Further expanding this, a negative inspection current instruction value Chcmd is inputted to the DAC 42, and a negative inspection current Ich is outputted from the DAC 42. In this case as well, since a temporal change of the difference value DIch can be obtained similar to FIG. 6, if the temporal change (square wave pulse) of the difference value DIch is acquired, and the fundamental frequency Fdi or the fundamental cycle TB thereof is obtained by frequency analysis, the bit to which the negative switching element, of the DAC 42, having caused "ON-failure" or "OFF-failure" corresponds can be detected.

Based on the above findings, in the gas sensor system 1 of the present embodiment, the instruction value generation part 47 including the above-described PID calculation part 4C2 generates a sequence of the above-described inspection current instruction value Chcmd(n). Specifically, the instruction value generation part 47 includes the short-circuit switch SW3 which causes a short-circuit between the second terminal T2 and the third terminal T3 (terminal 4T2 and terminal 4T3) in the sensor control circuit part 4, a constant input part 4C5, the PID calculation part 4C2, and an inspection coefficient setting part 4C6 in the control part 4C, and the like.

Then, when sequentially generating the inspection current instruction value Chcmd(n) in order to inspect the current converter 42, the short-circuit switch SW3 is turned on, and the detection cell voltage Vs to be inputted to the second AD converter 44 is forcibly set to zero. Accordingly, the detection cell voltage value Vsv which is the output of the second AD converter 44 is also set to zero (Vsv=0).

Meanwhile, a switching part 4C5K of the constant input part 4C5 is switched to connect a constant part 4C5C to the difference part 4C4 instead of the target Vs value input part 4C3. Accordingly, instead of the sensor voltage value Vsv, a predetermined input constant value N1=1 (when increasing in steps of a magnitude of 1 LSB) or N2=−1 (when decreasing in steps of a magnitude of 1 LSB) is inputted to the PID calculation part 4C2. Then, the difference values ΔVs(n), ΔVs(n+1), . . . outputted from the difference part 4C4 are also fixed to ΔVs(n)=ΔVs(n+1)=N1=1 or ΔVs(n)=ΔVs(n+1)=N2=−1.

In addition, the proportional coefficient Pc, the integration coefficient Ic, and the differential coefficient Dc, which are held in the respective coefficient holding parts 4C2PC, 4C2IC, and 4C2DC in the PID calculation part 4C2, are changed by the inspection coefficient setting part 4C6. Specifically, each coefficient in the above equation (1) is changed to Pc=0, Ic=1, and Dc=0. Then, the above equation (1) becomes J(n)=Iout(n)=ΔVs(n)+Iout(n−1). Here, since J(n−1)=Iout(n−1), the equation (1) becomes J(n)=ΔVs(n)+J(n−1).

Furthermore, the number n indicating the order is reset to n=1, and an initial value J(0) of the PID calculation value and an initial value Iout(0) of the I term are set to a predetermined value, for example, J(0)=Iout(0)=−1 (when increasing in steps of a magnitude of 1 LSB) or J(0)=Iout(0)=0 (when decreasing in steps of a magnitude of 1 LSB).

Accordingly, the first inspection current instruction value Chcmds is initially outputted as a PID calculation value J(1) from the PID calculation part 4C2 (for example, J(1)=Chcmd(1)=Chcmds=N1+J(0)=1+(−1)=0 or J(1)=Chcmd(1)=N2+J(0)=−1+0=−1). Thereafter, an inspection current instruction value Chcmd(n) composed of a signed 2M-bit (signed 14-bit) binary code that increases in steps of a magnitude of 1 LSB is sequentially generated as the PID calculation value J(n) (Chcmd(n)=1+Chcmd(n−1) or Chcmd(n)=−1+Chcmd(n−1)) every generation cycle Tc corresponding to a clock cycle.

When the generated inspection current instruction value Chcmd (n) reaches the final inspection current instruction value Chcmdf (Chcmd(n)=Chcmdf), the PID calculation part 4C2 stops the generation of the inspection current instruction value Chcmd(n). In addition, if N1=0.5 instead of N1=1 (Pc=Dc=0 and Ic=1 are the same), the rate of change of Chcmd(n) can be adjusted, for example, the value of Chcmd(n) increases by a magnitude of 1 LSB every 2Tc.

When the inspection current instruction value Chcmd(n), which changes (increases or decreases) in steps of a magnitude of 1 LSB from the first inspection current instruction value Chcmds to the final inspection current instruction value Chcmdf, is sequentially inputted to the DAC 42, if the DAC 42 has not failed, for example, as shown by the thick solid line in FIG. 5, an inspection current Ich that rises stepwise and linearly according to the inspection current instruction value Chcmd(n) is outputted from the DAC 42.

The inspection current instruction value Chcmd(n) is also inputted from the terminal 4T6 of the sensor control circuit part 4 via the connection wire 6 and the digital input terminal 5D to the CPU 5.

Then, if the input of the input constant value N1, N2 instead of the detection cell voltage value Vsv, the change of each coefficient Pc, etc., are performed as in the present embodiment, it is not necessary to generate the inspection current instruction value Chcmd separately from the calculation by the PID calculation part 4C2, and the inspection current instruction value Chcmd(n) which sequentially changes in steps of 1 LSB in a positive instruction value range PCE from the first inspection current instruction value Chcmds to the final inspection current instruction value Chcmdf can be easily obtained.

Next, detection of the inspection current Ich will be described with reference to FIG. 2. In the present embodiment, failure detection of the DAC 42 is performed in a state where the temperature of the sensor element part 3S (oxygen pump cell 14) is low, the sensor element part 3S (oxygen pump cell 14) is not activated, and the impedance of the sensor element part 3S (oxygen pump cell 14) is high, such as when the engine ENG is stopped, that is, in a state where the inspection current Ich does not flow toward the oxygen pump cell 14 (state where the magnitude of the inspection current Ich that branches at a branch node 7s and flows toward the oxygen pump cell 14 can be ignored).

Moreover, in the present embodiment, an inspection current detection part 7 which detects the magnitude of the inspection current Ich includes an inspection circuit part 7K provided outside the sensor control circuit part 4, and changeover switches SW1 and SW2 and a first AD converter 71 in the CPU 5, in the ECU 2. The inspection circuit part 7K includes a branch wire 7W, resistors 7R1 and 7Rp, and a protective capacitor 7Cp. Specifically, the branch wire 7W through which the inspection current Ich flows is provided so as to extend from the branch node 7s in a connection wire 5W1 connecting the first terminal T1 and the terminal 4T1 connected to the output terminal of the DAC 42. The branch wire 7W is connected to a GPIO terminal 5A of the CPU 5 via the first current detection resistor 7R1. The GPIO terminal 5A is connected to a ground potential via the changeover switch SW1 in the CPU 5, while being connected to a power supply voltage Vcc via the changeover switch SW2. The first current detection resistor 7R1 has a resistance value R1. Therefore, when inspecting a positive inspection current Ich, the positive inspection current Ich flows from the DAC 42 through the first current detection resistor 7R1 to the GPIO terminal 5A by turning on the changeover switch SW1 in a state where the changeover switch SW2 is turned off. In this case, the branch wire 7W has a potential corresponding to the magnitude of the inspection current Ich, specifically, a potential having a magnitude of Ich·R1. On the other hand, when inspecting a negative inspection current Ich, the negative inspection current Ich flows from the power supply potential Vcc through the GPIO terminal 5A and the first current detection resistor 7R1 toward the DAC 42 by turning on the changeover switch SW2 in a state where the changeover switch SW1 is turned off. In this case as well, the branch wire 7W has a potential corresponding to the magnitude of the inspection current Ich, specifically, a potential having a magnitude Vcc−Ich·R1 based on the power supply potential Vcc.

An analog input terminal 5C of the CPU 5 is connected to the branch wire 7W via a protective resistor 5p and a protective capacitor Cp. The analog input terminal 5C is connected to the first AD converter 71 in the CPU 5. Thus, the potential of the branch wire 7W is detected by the first AD converter 71, and an inspection current value Ichv(n) is calculated in consideration of the resistance R1 or the magnitudes of the resistance R1 and the power supply potential Vcc and is sequentially outputted.

Apart from this, as described above, the inspection current instruction value Chcmd(n) outputted by the PID calculation part 4C2 forming the instruction value generation part 47 is inputted to the CPU 5 through the connection wire 6. Therefore, by using the inspection current instruction value Chcmd(n), an expected value calculation part 8 of the CPU 5 sequentially calculates an inspection current expected value IMchv(n) which is an expected value of an inspection current value Ichv expected to be detected by the first AD converter 71 of the inspection current detection part 7 when there is no failure in the DAC 42. The inspection current expected value IMchv(n) corresponds to the magnitude of the inspection current Ich shown by the thick solid line in FIG. 5 and obtained when the DAC 42 is normal.

Next, a difference value acquisition part 9 of the CPU 5 sequentially acquires a difference value DIch(n) between the inspection current value Ichv(n) detected by the inspection current detection part 7 and the above inspection current expected value IMchv(n) calculated by the expected value calculation part 8, corresponding to the same inspection current instruction value Chcmd(n).

As already described with reference to FIG. 5 and FIG. 6, when there is no failure in the output stage of the DAC 42, the difference value DIch(n) is constantly 0±(DIch(n)=0±). On the other hand, when a switching element in the output stage of the DAC 42 has caused "ON-failure" or "OFF-failure", the difference value DIch(n) becomes a square wave pulse.

Therefore, a frequency analysis part 10FF in a failure detection part 10 performs frequency analysis on a temporal change of the difference value DIch(n) by an FFT analysis method and obtains the fundamental frequency Fdi (or fundamental cycle TB) of the square wave pulse formed by the difference value DIch(n). The magnitudes of the fundamental cycle TB and the fundamental frequency Fdi are different depending on the failed bit of the DAC 42. For example, as shown in FIG. 5 and FIG. 6, in the case where the generation cycle of the inspection current instruction value Chcmd(n) is set to Tc, when the 1st bit has caused a failure (ON-failure or OFF-failure), the fundamental cycle TB of the square wave pulse formed by the difference value DIch(n) has a magnitude of 2Tc (TB=2Tc).

When the DAC 42 is normal, the difference value DIch(n) becomes 0±, no square wave pulse is generated, and the fundamental cycle TB and the fundamental frequency Fdi are not obtained.

Therefore, a failure determination part 10D in the failure detection part 10, detects the presence/absence and magnitudes of the fundamental cycle TB and the fundamental frequency Fdi, whereby the presence/absence of a failure of the DAC 42 and the bit, among the plurality of bits forming the mantissa part, to which the switching element having caused "bit failure" corresponds, can be detected. When a positive inspection current instruction value is inputted, and, for example, the magnitude of the fundamental cycle TB is 2Tc (TB=2Tc), it can be determined that the positive switching element of the 1st bit of the DAC 42 has caused a bit failure (ON-failure or OFF-failure).

As can be understood from FIG. 6, when the square wave pulse formed by the difference value DIch(n) is a square wave pulse in which 0± and a positive value (0.98 µA in FIG. 6) alternate, it can be determined that "OFF-failure" has occurred. On the contrary, when the square wave pulse formed by the difference value DIch(n) is a square wave pulse in which 0± and a negative value (−0.98 µA in FIG. 6) alternate, it can be determined that "ON-failure" has occurred.

Thus, the sensor system 1 can detect a failure of the DAC 42, such as the presence/absence of a bit failure of the DAC 42 and the identification of the fault bit.

When any bit BI of the low-order bit group BL (1st to 7th bits in the present embodiment) has caused a bit failure in the DAC 42, the difference between the originally obtained current value and the actual current value is small, so that failure detection is easily influenced by noise. For example, as described above, when the positive switching element of the 1st bit in the DAC 42 has caused a bit failure, the difference between the originally obtained current value and the actual current value is a very small value of Io=0.98 µA, so that failure detection is easily influenced by noise. Therefore, by detecting, only about once or twice, the difference between the current value that should have been originally obtained and the current value that is actually obtained, it may be difficult to reliably determine the presence/absence of a bit failure (ON-failure or OFF-failure). However, after the difference between the current value that should have been originally obtained and the current value that is actually obtained is obtained a considerable number of times such that a frequency can be detected by frequency analysis, the influence of noise can be suppressed, and the presence/absence of a failure can be appropriately detected, by performing frequency analysis by the FFT analysis method in the frequency analysis part 10FF as described above.

Among the bits BI belonging to the low-order bit group BL, particularly, for the 1st bit (least significant bit) or the 2nd bit for which the difference between the current value that should have been originally obtained and the current value that is actually obtained becomes small and is easily influenced by noise, the method of the present embodiment is preferably used for detecting the presence/absence of a bit failure.

Figure 4:
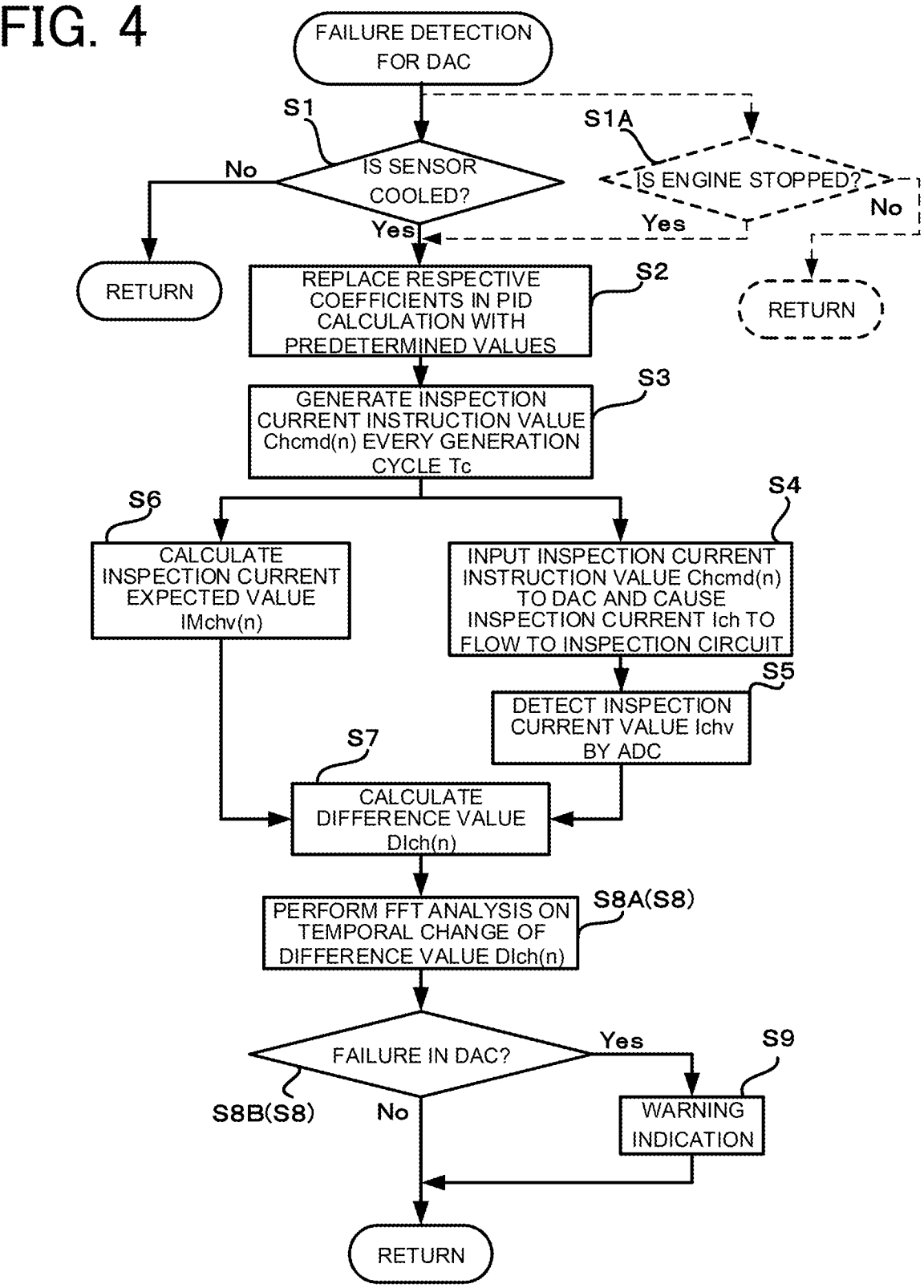
FIG. 4 is a flowchart showing the flow of processing for detecting a failure of a DAC according to the embodiment.

FIG. 4 is a flowchart showing the flow of processing for detecting a failure of the DAC 42 in the gas sensor system 1. As shown in FIG. 4, in the gas sensor system 1, when the system is started up, it is determined in step S1 whether or not the sensor element part 3S of the gas sensor 2 is cold. For example, the present state is a state where a sufficient amount of time has passed from the previous engine drive stop and the engine ENG has been sufficiently cooled (therefore, the sensor element part 3S of the gas sensor 2 has also been sufficiently cooled).

In the present embodiment, as described above, in a state where the inspection current Ich from the DAC 42 does not flow into the oxygen pump cell 14 via the first terminal T1 and the wire L1 and the impedance of the sensor element part 3S (oxygen pump cell 14) is high, the inspection current Ich is caused to flow to the inspection current detection part 7 through the branch node 7s to detect a failure of the DAC 42. Therefore, in step S1, it is determined whether or not the present state is a state where the sensor element part 3S (oxygen pump cell 14) has been sufficiently cooled and the impedance of the sensor element part 3S (oxygen pump cell 14) is high. If the present state is not a state where the impedance of the sensor element part 3S (oxygen pump cell 14) is high (if No), failure detection of the DAC 42 is not performed, and a return is made to normal control of the gas sensor 2. On the other hand, if the present state is a state where the impedance of the sensor element part 3S (oxygen pump cell 14) is high (Yes), the processing proceeds to step S2.

Examples of the method for determining whether or not the present state is a state where the impedance of the sensor element part 3S (oxygen pump cell 14) is high include a method in which it is determined whether or not a predetermined time (for example, 30 minutes) or longer has passed from the previous stop of the engine ENG, and a method in which the determination is performed based on the temperature of the cooling water of the engine ENG.

Next, in step S2, the third switch SW3 is turned on as described above. In addition, the switching part 4C5K of the constant input part 4C5 is switched to connect the constant part 4C5C to the difference part 4C4, and the difference values $\Delta Vs(n)$, $\Delta Vs(n+1)$, . . . are fixed to $\Delta Vs(n)=\Delta Vs(n+1)=N1=1$ or $N2=-1$. Furthermore, the inspection coefficient setting part 4C6 replaces the respective coefficients Pc, Ic, and Dc of the P term, the I term, and the D term, which are held in the coefficient holding parts 4C2PC, 4C2IC, and 4C2DC in the PID calculation part 4C2 of the control part 4C, with predetermined values (Pc=Dc=0, Ic=1). The number n indicating the order is reset to n=1, and the initial value J(0) of the PID calculation value is set to a predetermined value, for example, J(0)=1 or J(0)=0.

In a subsequent instruction value generation step S3, the inspection current instruction value Chcmd(n), which sequentially changes (increases or decreases) by a magnitude of 1 LSB every clock, is generated by the PID calculation part 4C2 every generation cycle Tc.

If the inspection current instruction value Chcmd(n) is generated by the PID calculation part 4C2 through change of each coefficient Pc, etc., it is not necessary to provide a circuit or the like for generating the inspection current instruction value Chcmd separately from the calculation by the PID calculation part 4C2, and the inspection current instruction value Chcmd(n) which sequentially changes in steps of 1 LSB can easily be obtained.

Further, in an input step S4, the generated inspection current instruction value Chcmd(n) is sequentially inputted to the DAC 42, and the inspection current Ich is outputted from the DAC 42 and caused to flow to the inspection circuit part 7K. Since the impedance of the oxygen pump cell 14 is high as described above, the inspection current Ich does not flow toward the oxygen pump cell 14.

Then, in an inspection current detection step S5, the inspection current value Ichv(n) of the inspection current Ich is detected by the first AD converter 71.

Meanwhile, in an expected value calculation step S6, the inspection current expected value IMchv(n), which is an expected value of the inspection current value Ichv(n) expected to be detected by the first AD converter 71, is separately and sequentially calculated from the inspection current instruction value Chcmd(n) generated in the instruction value generation step S3.

Then, in a difference value acquisition step S7, the difference value DIch(n) between the inspection current value Ichv(n) and the inspection current expected value IMchv(n) corresponding to the same inspection current instruction value Chcmd(n) is sequentially calculated.

As described above, when the DAC 42 is normal, the difference value DIch(n) is constantly 0 (DIch(n)=0). This is because no difference occurs between the inspection current value Ichv(n) and the inspection current expected value IMchv(n). On the other hand, when a bit failure has occurred in each bit forming the mantissa part of the DAC 42, the temporal change of the difference value DIch(n) becomes a square wave pulse (see FIG. 6).

Therefore, in a frequency analysis step S8A of a failure detection step S8, FFT analysis is performed on the temporal change of the difference value DIch(n), and the fundamental frequency Fdi (or fundamental cycle TB) of the square wave pulse formed by the difference value DIch(n) is obtained.

Furthermore, in a failure determination step S8B of the failure detection step S8, the presence/absence of a failure of the DAC 42 is determined. If the fundamental frequency Fdi (or fundamental cycle TB) is not obtained, it is determined that the DAC 42 is normal. On the other hand, if the fundamental frequency Fdi (or fundamental cycle TB) is obtained, it is determined that the DAC 42 has caused a bit failure. In addition, which bit of the plurality of bits forming the mantissa part is the fault bit (for example, in the case of FIG. 6, it is the 1st bit) is detected based on the magnitude of the fundamental frequency Fdi (or fundamental cycle TB).

Then, if a failure of the DAC 42 has been detected (Yes), the processing proceeds to a warning display step S9, and a warning (serviceman call, etc.) indicating that the DAC 42 has caused a bit failure and indicating the fault bit is displayed toward the driver, and a return is made to normal control of the gas sensor 2. On the other hand, if no failure of the DAC 42 has been detected (No), a return is made to normal control of the gas sensor 2 without performing the warning display step S9.

Thus, a failure detection method, for the sensor system 1, which allows a failure of the DAC 42, such as the presence/absence of a bit failure of the DAC 42 and the identification of the failed bit, to be appropriately detected, is provided.

In particular, in the DAC 42, for any bit BI of the low-order bit group BL (1st to 7th bits in the present embodiment) which is easily influenced by noise, the influence of noise is suppressed and the presence/absence of a failure can be appropriately detected.

While the present invention has been described above based on the embodiment, it should be understood that the present invention is not limited to the above embodiment but can be applied with modifications appropriately made thereto without departing from the scope of the gist of the present invention.

For example, in the embodiment, the air-fuel ratio sensor (full-range air-fuel ratio sensor) which detects the oxygen concentration (air-fuel ratio) of the exhaust gas EG is used as the gas sensor 2. However, the "gas sensor" is not limited to the air-fuel ratio sensor, and may be a NOx sensor which detects the concentration of nitrogen oxides (NOx) as a specific gas concentration, or the like. Furthermore, the present invention is not limited to the gas sensor, and may be applied to a sensor system that includes a sensor element to which a control current is inputted, a DAC which outputs the control current, and a control part which inputs the control current to the DAC.

In the above-described embodiment, in detecting a failure of the gas sensor system 1, it is determined in step S1 (see FIG. 4) whether or not the sensor element part 3S of the gas sensor 2 is cold.

However, in detecting a failure of a sensor system, in the case of performing failure detection for another sensor system including a sensor for which it is unnecessary to consider cooling of the sensor due to, for example, the absence of a part corresponding to the sensor element part 3S, steps S2 to S9 may be executed, for example, as shown by the broken line in FIG. 4, while the engine ENG having this sensor system mounted thereon is stopped (Yes in step S1A). In this case, the failure detection method of the present technology is executed not while the engine ENG having the sensor system mounted thereon is operating such as while the vehicle equipped with the engine ENG is driven, but while the engine ENG is stopped. Therefore, failure detection of the sensor system can be performed without influencing the operation of the engine ENG.

REFERENCE SIGNS LIST

1 Gas sensor system (sensor system)
2 ECU
3 Gas detection part (sensor)
3S Sensor element part (sensor element)
14 Oxygen pump cell
22 Second detection electrode
24 Oxygen concentration detection cell
Vs Detection cell voltage (sensor volage)
Vsv Detection cell voltage value
4 Sensor control circuit part
4C Control part
Ipcmd Control current instruction value
Chcmd, Chcmd(n) Inspection current instruction value
Chcmds First inspection current instruction value
Chcmdf Final inspection current instruction value
Tc Generation cycle (cycle) (of inspection current instruction value)
42 DA converter
BI Bit
BU High-order bit group
BL Low-order bit group
44 Second AD converter
47 Instruction value generation part
5 CPU
7 Inspection current detection part
7K Inspection circuit part
Ich Inspection current
Ichv Inspection current value
71 First AD converter
8 Expected value calculation part
IMchv Inspection current expected value
9 Difference value acquisition part
Dich Difference value (between the inspection current value and the inspection current expected value)
10 Failure detection part
10FF Frequency analysis part
Fdi Fundamental frequency (on a temporal change of the difference value)
TB Fundamental cycle (on the temporal change of the difference value)
10D Failure determination part
S3 Instruction value generation step
S4 Input step
S5 Inspection current detection step
S6 Expected value calculation step
S7 Difference value acquisition step
S8 Failure detection step
S8A Frequency analysis step (failure detection step)
S8B Failure determination step (failure detection step)

What is claimed is:

1. A sensor system comprising:
a sensor element to which a control current is input;
a DA converter configured to output the control current toward the sensor element;
a control part configured to generate a control current instruction value corresponding to a magnitude of the control current and to input the control current instruction value to the DA converter;
an instruction value generation part configured to sequentially generate an inspection current instruction value per every predetermined generation cycle, said inspection current instruction value being input to the DA converter and changing in steps of a magnitude of 1 LSB from a first inspection current instruction value generated first to a final inspection current instruction value generated last;
an inspection current detection part configured to detect an inspection current value of an inspection current output from the DA converter to which the inspection current instruction value is input;
an expected value calculation part configured to calculate an inspection current expected value, which is an expected value of the inspection current value expected to be detected by the inspection current detection part, by the inspection current instruction value being input to the DA converter;
a difference value acquisition part configured to acquire a difference value between the detected inspection current value and the calculated inspection current expected value, corresponding to the same inspection current instruction value; and a failure detection part configured to detect a failure of a bit of the DA converter by frequency analysis of a temporal change of the sequentially obtained difference value.

2. The sensor system according to claim 1, wherein the bit whose failure is detected by the failure detection part is a bit belonging to a low-order bit group in the DA converter.

3. The sensor system according to claim 2, wherein
the sensor element has a sensor output terminal at which a sensor voltage is generated,
the sensor system further comprises an AD converter configured to sequentially convert the sensor voltage generated at the sensor output terminal into a sensor voltage value,
the control part includes a PID calculation part configured to generate the control current instruction value by PID calculation using the sensor voltage value, and
the instruction value generation part includes
an input part configured to input a predetermined input constant value, instead of the sensor voltage value, to the PID calculation part of the control part, and
an inspection coefficient setting part configured to set a coefficient Pc of a P term and a coefficient Dc of a D term in the PID calculation by the PID calculation part to 0, and to set a coefficient Ic of an I term to a magnitude which allows the inspection current instruction value, which is sequentially changed in steps of a magnitude of 1 LSB, to be output from the PID calculation part.

4. The sensor system according to claim 1, wherein
the sensor element has a sensor output terminal at which a sensor voltage is generated,
the sensor system further comprises an AD converter configured to sequentially convert the sensor voltage generated at the sensor output terminal, into a sensor voltage value,
the control part includes a PID calculation part configured to generate the control current instruction value by PID calculation using the sensor voltage value, and
the instruction value generation part includes
an input part configured to input a predetermined input constant value, instead of the sensor voltage value, to the PID calculation part of the control part, and
an inspection coefficient setting part configured to set a coefficient Pc of a P term and a coefficient Dc of a D term in the PID calculation by the PID calculation part to 0, and to set a coefficient Ic of an I term to a magnitude which allows the inspection current instruction value, which is sequentially changed in steps of a magnitude of 1 LSB, to be output from the PID calculation part.

5. A failure detection method for a sensor system including a sensor element to which a control current is input, a DA converter configured to output the control current toward the sensor element, and a control part configured to generate a control current instruction value corresponding to a magnitude of the control current and input the control current instruction value to the DA converter, the failure detection method comprising:
instruction value generating of sequentially generating an inspection current instruction value per every predetermined generation cycle, said inspection current instruction value changing in steps of a magnitude of 1 LSB from a first inspection current instruction value generated first to a final inspection current instruction value generated last;
inputting of sequentially inputting the inspection current instruction value to the DA converter;
inspection current detecting of detecting an inspection current value of an inspection current output from the DA converter;
expected value calculating of calculating an inspection current expected value, which is an expected value of the inspection current value expected to be detected by the inspection current detection part, by the inspection current instruction value being input to the DA converter;
difference value acquiring of acquiring a difference value between the detected inspection current value and the calculated inspection current expected value, corresponding to the same inspection current instruction value; and
failure detecting of detecting a failure of a bit of the DA converter by frequency analysis of a temporal change of the sequentially obtained difference value.

6. The failure detection method for the sensor system according to claim 5, wherein the bit whose failure is detected in the failure detecting is a bit belonging to a low-order bit group in the DA converter.

7. The failure detection method for the sensor system according to claim 6, wherein
the sensor element has a sensor output terminal at which a sensor voltage is generated,
the sensor system includes an AD converter configured to sequentially convert the sensor voltage generated at the sensor output terminal, into a sensor voltage value,
the control part includes a PID calculation part configured to generate the control current instruction value by PID calculation using the sensor voltage value,
the instruction value generating includes
inputting a predetermined input constant value, instead of the sensor voltage value, to the PID calculation part of the control part, and
setting a coefficient Pc of a P term and a coefficient Dc of a D term in the PID calculation to 0, and setting a coefficient Ic of an I term to a magnitude which allows the inspection current instruction value, which is sequentially changed in steps of 1 LSB, to be output from the PID calculation part, and
the PID calculation part is caused to sequentially generate the inspection current instruction value.

8. The failure detection method for the sensor system according to claim 7, wherein the failure detection method is executed while an internal combustion engine having the sensor system mounted thereon is stopped.

9. The failure detection method for the sensor system according to claim 6, wherein the failure detection method is executed while an internal combustion engine having the sensor system mounted thereon is stopped.

10. The failure detection method for the sensor system according to claim 5, wherein
the sensor element has a sensor output terminal at which a sensor voltage is generated,
the sensor system includes an AD converter configured to sequentially convert the sensor voltage generated at the sensor output terminal, into a sensor voltage value,
the control part includes a PID calculation part configured to generate the control current instruction value by PID calculation using the sensor voltage value, the instruction value generating includes
inputting a predetermined input constant value, instead of the sensor voltage value, to the PID calculation part of the control part, and setting a coefficient Pc of a P term and a coefficient Dc of a D term in the PID calculation to 0, and setting a coefficient Ic of an I term to a magnitude which allows the inspection current instruction value, which is sequentially changed in steps of 1 LSB, to be output from the PID calculation part, and the PID calculation part is caused to sequentially generate the inspection current instruction value.

11. The failure detection method for the sensor system according to claim 5, wherein the failure detection method is executed while an internal combustion engine having the sensor system mounted thereon is stopped.

12. The failure detection method for the sensor system according to claim 10, wherein the failure detection method is executed while an internal combustion engine having the sensor system mounted thereon is stopped.

* * * * *